United States Patent
Yang et al.

(10) Patent No.: US 11,056,214 B2
(45) Date of Patent: Jul. 6, 2021

(54) DUAL SAMPLE MELTING CURVE CLUSTER AND COST ANALYSIS

(71) Applicant: Canon U.S. Life Sciences, Inc., Rockville, MD (US)

(72) Inventors: Yang Yang, Sunnyvale, CA (US); Bradley Scott Denney, Irvine, CA (US); Attaullah Seikh, Irvine, CA (US)

(73) Assignee: Canon U.S.A., Inc., Melville, NY (US)

( * ) Notice: Subject to any disclaimer, the term of this patent is extended or adjusted under 35 U.S.C. 154(b) by 402 days.

(21) Appl. No.: 15/631,794

(22) Filed: Jun. 23, 2017

(65) Prior Publication Data

US 2018/0011969 A1     Jan. 11, 2018

Related U.S. Application Data

(60) Provisional application No. 62/353,615, filed on Jun. 23, 2016.

(51) Int. Cl.
| | |
|---|---|
| *G16B 40/00* | (2019.01) |
| *G06F 17/18* | (2006.01) |
| *G01N 21/64* | (2006.01) |
| *G01N 25/04* | (2006.01) |
| *C12Q 1/6844* | (2018.01) |
| *G16B 20/20* | (2019.01) |
| *G16B 40/30* | (2019.01) |

(52) U.S. Cl.
CPC .......... *G16B 40/00* (2019.02); *C12Q 1/6844* (2013.01); *G01N 21/6428* (2013.01); *G01N 25/04* (2013.01); *G06F 17/18* (2013.01); *G16B 20/20* (2019.02); *G16B 40/30* (2019.02); *G01N 2021/6439* (2013.01)

(58) Field of Classification Search
None
See application file for complete search history.

(56) References Cited

U.S. PATENT DOCUMENTS

| | | | |
|---|---|---|---|
| 8,145,433 B2 | 3/2012 | Boles et al. | |
| 8,296,074 B2 | 10/2012 | Palais et al. | |
| 8,483,972 B2 | 7/2013 | Kanderian | |
| 8,606,527 B2 | 12/2013 | Houser | |
| 2011/0105345 A1 | 5/2011 | Cheng et al. | |
| 2011/0238323 A1 | 9/2011 | Robbins et al. | |
| 2014/0272927 A1 | 9/2014 | Coursey et al. | |

OTHER PUBLICATIONS

Dhakal, Rajat, et al. "Genotyping of dairy *Bacillus licheniformis* isolates by high resolution melt analysis of multiple variable number tandem repeat loci." Food microbiology 34.2 (2013): 344-351.*
Liu, Ran, et al. "Multicolor melting curve analysis-based multilocus melt typing of vibrio parahaemolyticus." PloS one 10.9 (2015): e0136998.*
Francisco, Alexandre P., et al. "Global optimal eBURST analysis of multilocus typing data using a graphic matroid approach." BMC bioinformatics 10.1 (2009): 152.*
User Guide of Life Technologies Corporation: Applied Biosystems High Resolution Melt Software for QuantStudio™ 12K Flex Real-Time PCR System.
Nellåker: "Mixture models for analysis of melting temperature data," BMC Bioinformatics 2008, 9:370.
Dwight et al.: "uAnalyze: Web-Based High-Resolution DNA Melting Analysis with Comparison to Thermodynamic Predictions," IEEE/ACM Transactions on Computational Biology and Bioinformatics, vol. 9, No. X, XXXXXXX 2012.
Dwight et al.: "uMELT: prediction of high-resolution melting curves and dynamic melting profiles of PCR products in a rich web application," Bioinformatics Applications Note, vol. 27 No. 7 2011, pp. 1019-1020.

* cited by examiner

*Primary Examiner* — G Steven Vanni
(74) *Attorney, Agent, or Firm* — Canon U.S.A., Inc. IP Division

(57) ABSTRACT

The present invention relates to methods and systems for the analysis of nucleic acids present in biological samples, and more specifically, relates to clustering melt curves derived from high resolution thermal melt analysis performed on a sample of nucleic acids, the resulting clusters being usable, in one embodiment, for analyzing the sequences of nucleic acids and to classify their genotypes that are useful for determining the identity of the genotype of a nucleic acid that is present in a biological sample.

17 Claims, 12 Drawing Sheets

```
Algorithm determine K_opt
    Input:  dissimilarity KLD based on KL-divergence,
            dissimilarity threshold θ.
    Output: best cluster number K_opt.
    Init:   has_id(1:8) = 0;
            K_opt= 0;

for i = 1:8 // for each curve
        if hasid(i) == 0 // if i has not been assigned to a cluster
            K_opt= K_opt+ 1;
            hasid(i) = 1;
            for j = i+1:8
                if (KLD(i,j)) <= θ && hasid(j) == 0
                    hasid(j) = 1;
                end
            end
        end
    end
```

DUAL SAMPLE MELTING CURVE CLUSTER AND COST ANALYSIS

PRIORITY CLAIM AND INCORPORATION BY REFERENCE

This application claims the benefit of priority to U.S. Provisional Patent Application Ser. No. 62/353,615 filed Jun. 23, 2017, which is incorporated herein in its entirety. This application references and makes use of various techniques and features described in the following US patents and Currently pending patent applications: U.S. Pat. No. 8,283,972, currently pending U.S. patent application Ser. No. 13/937,522 which is continuation of the '972 Patent, U.S. Pat. Nos. 8,145,433, 8,606,529 and currently pending U.S. patent application Ser. No. 14/191,647. Reference is also made to U.S. patent application Serial No. to be assigned filed concurrent herewith on Jun. 23, 2017 (identified as Ser. No. 15/631,832). Each of the above referenced US patents and pending patent applications are incorporated herein by reference in their entireties.

BACKGROUND

Field of the Invention

The present invention relates to methods for the analysis of nucleic acids present in biological samples, and more specifically to determining an optimal cluster from a group of candidate clusters and using the optimal cluster to identify one or more properties of the nucleic acids.

Description of Related Art

The detection and identification of nucleic acids is central to medicine, forensic science, industrial processing, crop and animal breeding, and many other fields. A number of high throughput approaches to performing polymerase chain reactions (PCR) and other amplification reactions to identify and detect characteristics of nucleic acids have been developed. One example involves amplification reactions in devices, including, for example, microfluidic devices, as well as methods for detecting and analyzing amplified nucleic acids in or on the devices. These devices enable further characterization of the amplified DNA molecules contained therein. One method of characterizing the DNA is to examine the DNA's dissociation behavior as the DNA transitions from double stranded DNA (dsDNA) to single stranded DNA (ssDNA). The process of causing DNA to transition from dsDNA to ssDNA with increasing temperature is sometimes referred to as a "high-resolution temperature (thermal) melt (HRTm)" process, or simply a "high-resolution melt" process.

Melting profile analysis is an important technique for analyzing nucleic acids. In some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has "melted" or denatured, i.e., unzipped, partially or completely. Thus, by measuring the dye fluorescence as a function of temperature, information is gained regarding the length of the duplex, the GC content or even the exact sequence.

Some nucleic acid assays require differentiation between potential genotypes within a class of known genotypes. Generally, for thermal melt analysis, researchers will visually inspect a thermal melt profile to determine the melting temperature of the nucleic acid in the sample. However, some nucleic acid assays require identification of a single nucleotide change where the difference in melting temperature ($T_m$) between the wild type nucleic acid and a mutant nucleic acid is quite small (e.g. less than 0.25° C.). Melt curves generally show fluorescence versus temperature or the derivative of fluorescence versus temperature acting as a unique signature or profile for each genotype. In this instance, an operator may identify a genotype by visually comparing dynamic temperature profiles that yield a unique signature or profile for each genotype. Typically an operator identifies the genotype by visually comparing these dynamic signatures. However, it is much simpler to visually classify and observe the degree of separation of different genotypes using clustering of melting curves or data clustering of data points. Furthermore, if a data point or curve is not contained within any clusters of previously identified genotypes, this may indicate the discovery of a new mutation or genotype. Examples of genotyping classification includes identifying the genotype as homozygous wildtype (WT), heterozygous (HE) or homozygous mutant (HM) depending on the alleles that make up the DNA. Data points or curves from the same genotype form a cluster. In genotyping or any classification problem, it is important for clusters representing different genotypes or classes to be different from each other to minimize the likelihood of misclassification. Currently the visual representation of different high resolution melts is displayed as dynamic curves to the user. Representing each dynamic curve as a data point is sometimes useful because in a classification problem such as this, the position of a point relative to genotype clusters obtained from a training set of known genotypes tells the user which cluster a DNA sample of unknown genotype likely belongs to along with a level of confidence.

It is desirable to appropriately cluster the melt curves into groups having similar curve properties. Melting curves that are clustered together are indicative of a similar property or genotype being shared among the curves of the cluster. Moreover, clustering the melt curves into groups makes the analysis of a large number of melt curves easier. One manner of clustering that has been applied to groups of melt curves use distance-based metrics which are sensitive to the scale of the curves. However, a drawback associated with the methods using distance based metrics is it tends to ignore the fundamental stochastic nature of the reactions that create the melt curves. Additionally, it may treat errors in non-informative parts of the melt curve (i.e. temperatures outside the melting region) equally as errors in the informative parts of the curve (i.e. the melting temperature region). Another clustering methods start with random seeds and stops when predetermined criteria (e.g. within group sum of square errors) have been met. The drawback here is that the resulting clusters generated reach the local optimum and not a global optimum. Yet another method of clustering use a hierarchical clustering method which means that that the technique is either top-down or bottom up and necessarily depend on the previous clustering result. Thus, there is either a divisive step for a top-down hierarchical clustering method or a agglomerative step for the bottom-up clustering method. The drawback associated with hierarchical clustering is that it may not find the global optimum. It is therefore desirable to provide a method of clustering melt curves that remedy the deficiency of the above discussed clustering methods. A system and method according to invention principles remedies these deficiencies.

SUMMARY OF THE INVENTION

The present invention relates to methods and systems for the analysis of nucleic acids and the identification of genotypes present in biological samples. More specifically, embodiments of the present invention relate to clustering melt curves derived from high resolution thermal melt analysis performed on a sample of nucleic acids, the resulting clusters being usable, in one embodiment, for analyzing the sequences of nucleic acids and to classify their genotypes that are useful for determining the identity of the genotype of a nucleic acid that is present in a biological sample.

In one embodiment, a method of clustering a set of melt curves generated by high resolution melt analysis is provided. The method includes setting a threshold representing an acceptable level of dissimilarity between candidate curves to be included in a cluster. Selecting an optimal number of clusters in which the set of melt curves are to be clustered based on a cluster quality measure using the calculated dissimilarity levels. Generating a number of clusters equal to the selected optimal number of clusters and displaying the generated number of clusters to a user in a user interface enabling receipt of input confirming the generated number of clusters is accurate.

In another embodiment, a set of clusterings is displayed to the user through a user interface whereby the set of clusters displayed shows clustering results using differing numbers of clusters. In some of these embodiments, all numbers of clusterings are shown from 1 cluster to the case where every curve is in its own cluster. Additionally, an optimal number of clusters is determined and the user interface may indicate one or more clusterings as being optimal.

In a further embodiment, a candidate set of recommended clusters are generated by grouping the selected optimal cluster number of cluster number one less than the selected optimal cluster number and a cluster number one more than the optimal cluster number. In certain embodiments, the group of recommended clusters is displayed in an ordered list. In another embodiment, the group of recommended clusters is displayed using a predetermined visual indicator that is different than a visual indicator used for other cluster groups.

In another embodiment, the user interface including the group of recommended includes selectable image elements enabling the user to select at least one cluster from the group of recommended clusters as a selected cluster.

In another embodiment, data representing individual melt curves contained in each cluster of the optimal number of clusters is provided to a system which uses the individual melt curve data to derive at least one characteristic (e.g. genotype) associated with a nucleic acid contained in the sample that underwent melt analysis.

BRIEF DESCRIPTION OF THE FIGURES

The accompanying drawings, which are incorporated herein and form part of the specification, illustrate various embodiments of the present invention.

FIG. 4 illustrates a clustering algorithm according to invention principles.

DETAILED DESCRIPTION

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

Figure 1:
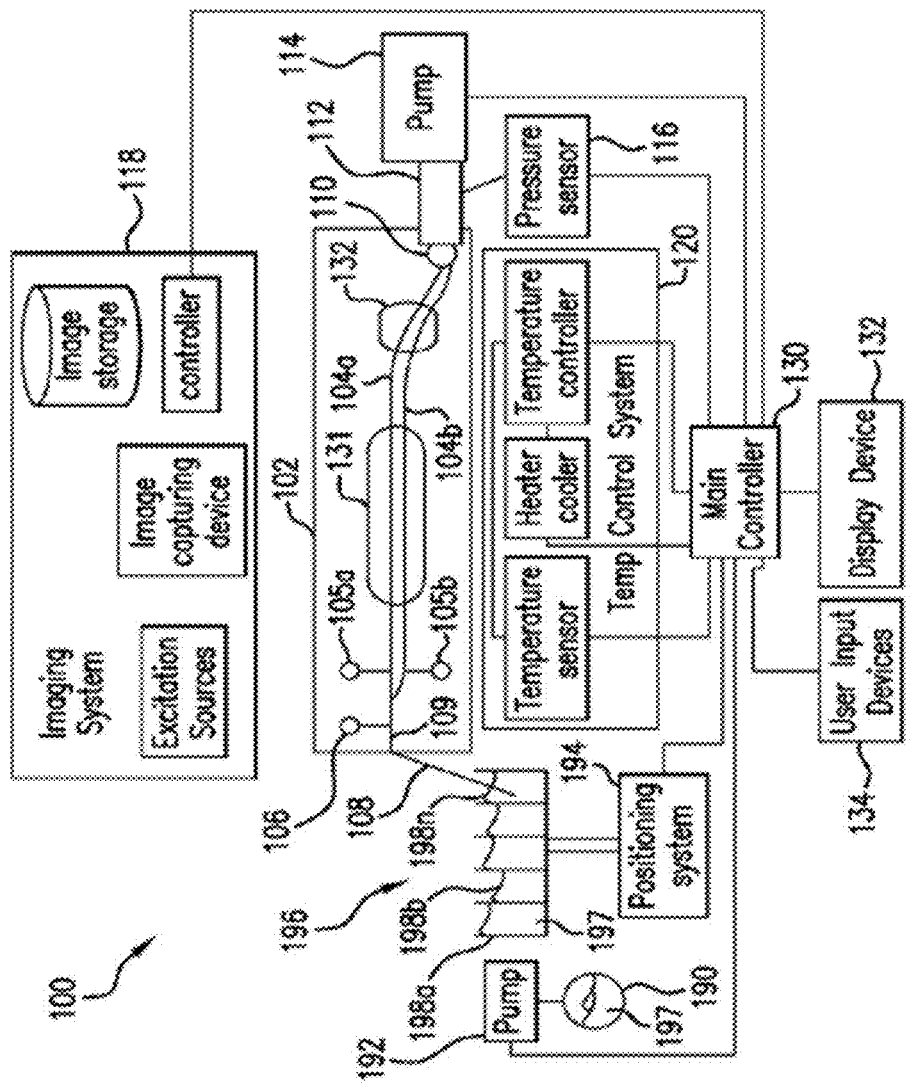
FIG. 1 illustrates a genetic analyzer device according to invention principles.

An apparatus and system for identifying a nucleic acid in a sample including at least one unknown nucleic acid. An example of a suitable system in accordance with some aspects of the invention is illustrated in connection with FIG. 1. As illustrated in FIG. 1, system 100 may include a device 102. Device 102 may be a microfluidic device. Device 102 may include one or more channels 104 each having a heating element, the temperature of which is selectively configurable using one or more heating parameters. Channels 104 may be, for example, microfluidic channels. In one embodiment, the one or more heating parameters may be predetermined and set in advance by control application. In another embodiment, the one or more heating parameters may be selectively calculated and determined in response to data derived from one or more reactions chemical and/or physical reactions occurring or which have occurred on a sample contained in the respective channels 104. In the examples shown, device 102 includes two channels, channel 104a and channel 104b each of them including a respective heating element and able to receive one or more samples thereon and support various reaction processing on the samples contained therein. Although only two channels are shown in the exemplary embodiment, it is contemplated that device 102 may have fewer than two or more than two channels. For example, in some embodiments, device 102 includes eight channels 104.

In one embodiment, device 102 may include a single DNA processing zones in which DNA amplification occurs prior to high resolution thermal melt processing which yields a dynamic signal such as a melt curve showing the relationship of fluorescence intensity level and temperature. In the DNA processing zone, a control application selectively controls a temperature of the respective heating element within the zone according to parameters specific to the type of reaction occurring at a given time. For example, during amplification, a temperature of the heating element in at a first time period may be different from a temperature at a second time period when melt processing is occurring. In operation and during DNA processing, a series of pumps is selectively controlled by an edge control algorithm which controls the flow of blanking fluid through the one or more channels 104. The edge control system, in real-time, ensures that the sample being processed remains within a specified region of interest (ROI) so that appropriate temperature changes can be applied by the heating elements within respective channels and fluorescence levels can be captured.

In another embodiment, the device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 1, PCR zone 131 includes a first portion of channels 104 and melt zone 132 includes a second portion of channels 104, which is downstream from the first portion. In these zones, a control application selectively controls a temperature of the respective heating element within the respective zones 131 and 132 according to parameters specific to the type of reaction occurring in the respective zones 131 and 132. For example, a temperature of the heating element in the DNA amplification zone 131 may be set differently from a temperature of the DNA melt zone 132. In operation and during DNA processing, a series of pumps is selectively controlled by an edge control algorithm which controls the flow of blanking fluid through the channels 104. The edge control system, in real-time, ensures that the sample being processed remains within a specified region of interest (ROI) so that appropriate temperature changes can be applied by the heating elements within respective channels and fluorescence levels can be captured.

In one embodiment, device 102 may also include a sipper 108. Sipper 108 may be in the form of a hollow tube. Sipper 108 has a proximal end that is connected to an inlet 109 which inlet couples the proximal end of sipper 108 to one or more channels 104. Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the one or more channels 104, system 100 may include a well plate 196 that includes a plurality of wells 198, at least some of which contain a sample solution (e.g., a solution containing a DNA sample). In the embodiment shown, well plate 196 is connected to a positioning system 194 which is connected to a main controller 130.

Main controller 130 is a central processing unit and includes hardware for performing a plurality of calculations and controlling the complete operational aspects of apparatus 100 and all components therein. Positioning system 194 may include a positioner for positioning well plate 196, a stepping drive for driving the positioner, and a positioning controller for controlling the stepping drive.

To introduce a sample solution into the one or more channels 104, the positioning system 194 is controlled to move well plate 196 such that the distal end of sipper 108 is submerged in the sample solution stored in one of the wells 198. FIG. 1 shows the distal end of 108 being submerged within the sample solution stored in well 198n. In order to force the sample solution to move up the sipper and into the channels 104, a vacuum manifold 112 and pump 114 may be employed. During DNA processing, the pump 114 is controlled by an edge control algorithm which controls the flow of blanking fluid through one or more channels 104 by monitoring the edge of the blanking fluid at separate imaging location 132 or alternatively within the processing zone 131. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels one or more 104. Additionally, this causes the reagents in wells 106 and 105 to flow into a channel. Accordingly, pump 114 functions to force a sample solution and real-time PCR reagents to flow through one or more channels 104. In operation where there is a single DNA processing zone 131, PCR occurs first followed by melt processing. In another embodiment having two separate DNA processing zones, melt zone 132 is located downstream from PCR zone 131. Thus, in this embodiment, a sample solution will flow first through the PCR zone and then through the melting zone. In embodiments having a single DNA processing zone, the sample solution will flow through the DNA processing zone 131 where it will undergo PCR and HRM, with a leading edge of the sample solution entering a separate imaging location 132. The embodiments having a single DNA processing zone are described in details in US Patent Application No. 2014/0272927 which is incorporated by reference herein in its entirety.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. In order to achieve PCR for a DNA sample during amplification processing in the DNA processing zone (either the PCR zone in a two zone system or single DNA processing zone 131), the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples while in the DNA processing zone and undergoing PCR and following when the sample undergoes melt processing. Main controller 130 may be connected to a display device for displaying a graphical user interface. Main controller 130 may also be connected to user input devices 134, which allow a user to input data and commands into main controller 130.

To monitor the PCR process and the melting process that occur in the single DNA processing zone 131 (or when two zones are present, PCR zone 131 and melt zone 132), system 100 may include an imaging system 118. Imaging system 118 may include an excitation source, an image capturing device, a controller, and an image storage unit.

To achieve this goal, the device executes melt processing algorithm which controls the components discussed above to perform melt processing on a plurality of samples in individual channels of a device 102. The main controller 130 causes receives data representing a fluorescence level over a period time at different temperature levels. The result is a melt curve showing this relationship. By analyzing the melt curve, at least one characteristic of the nucleic acid can be identified. In one embodiment, the at least one characteristic is one of a type of nucleic acid and a genotype of the nucleic acid. This characteristic determination is based on the temperature at which the fluorescence level drops indicating denaturation of the nucleic acid at that temperature. These values can be compared to known value to identify the at least one characteristic. To improve the ability of the device to identify the characteristic associated with the sample, a clustering algorithm according to invention principles is stored on a storage device which can be accessed and executed by main controller 130. In certain embodiments, the clustering algorithm may be embodied as any one of an executable application and a module, or a combination of both. Further, the remaining description may use the terms algorithm, application and/or module interchangeably but each refers to a set of instructions stored on a storage device (memory) that when executed by one or more controllers or central processing units, operate to control various elements of the system to act in a desired manner to achieve a desired goal.

Figure 2:
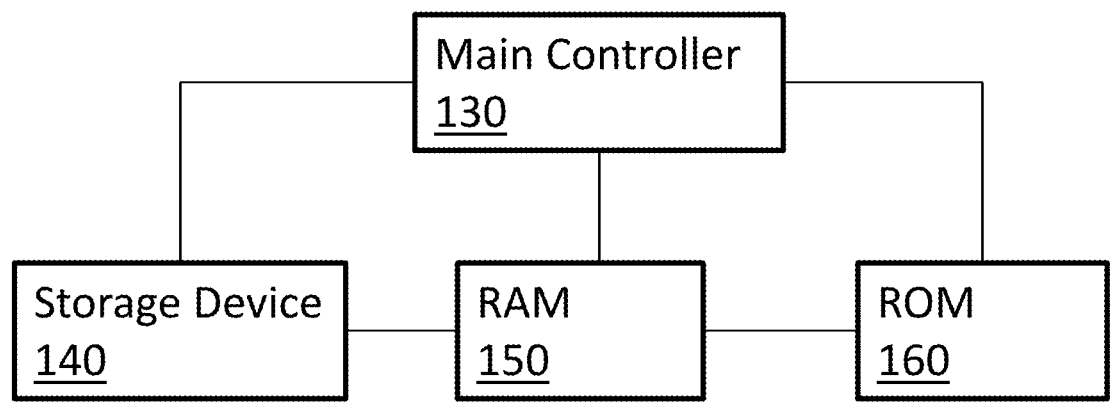
FIG. 2 illustrates certain components of the genetic analyzer shown in FIG. 1 according to invention principles.

The clustering algorithm advantageously improves grouping of melt curves generated during a single melt processing run on a particular device by improving the manner in which the resulting melt curves are grouped together thereby providing a user with an optimal number of clusters. The optimal number of clusters satisfy a predetermined cluster quality value which indicates that the curves contained within each cluster are similar to one another. Put another way, the curves within each cluster have a low dissimilarity level between one another. FIG. 2 illustrates additional hardware embodied within the system 100 shown in FIG. 1 that act on or are controlled by the execution of the clustering algorithm.

The main controller 130 includes one or more central processing units which are hardware circuits that execute instructions stored in one of memory 140, RAM 150 or ROM 160. The main controller 130 may include a central processing unit (CPU), one or more general-purpose microprocessor(s), application-specific microprocessor(s), and/or special purpose microprocessor(s), or some combination of such processing components. The main controller 130 may retrieve the instructions from the memory 140, RAM 150 and/or ROM 160, an internal register, or an internal cache. The main controller 130 then decodes and executes the instructions. Then, the main controller 130 writes one or more results to the storage device 140, RAM 150, the internal register, or the internal cache. The main controller 130 may provide the processing capability to execute the operating system, programs, user and application interfaces, and any other functions of the device 100.

In one embodiment, the clustering algorithm is embodied as a clustering application and may be stored in one of storage device 140 and be selectively executed by the main controller 130 to load, into specifically addressed sectors of RAM 150 (or other work area memory) the instructions for generating cluster data having a number of clusters up to a number of melt curves produced by melt processing and identifies an optimal cluster number in which each melt curve can be grouped into. Melt curves that are grouped together into a cluster having a cluster center value typically share similar properties and/or genotypes so this grouping reduces an amount of time needed to analyze a number of different melt curves. Each melt curve is treated as a probability distribution and a divergence measuring method is used to measure and generate a dissimilarity value between a pair melt curves. The dissimilarity value for each pair may be calculated only once and stored in memory as a data structure which can be continually referenced by the clustering algorithm when both determining the optimal number of clusters and grouping the melt curves into respective clusters. Further, the clustering algorithm enables a global optimum clustering solution to be produced because of the predetermined (e.g. small) number of curves for which clustering need be performed. In one embodiment, the predetermined number of curves equals a number of channels and/or wells of a device. In another embodiment, the predetermined number of curves ranges between one and eight based on a device having eight channels. In other embodiments, the predetermined number of curves ranges between 24 and 384. In further embodiments, the number of curves is equal to a number of wells included on a well plate such as 6, 12, 24, 48, 72, 96 and 384. In other embodiments, the predetermined number of curves may be equal to any number in a range between zero and a maximum number of channels/wells in the device. For example, if the device is a well plate including 96 wells, the predetermined number of curves may be any number of curves ranging between 1 and 96. Additionally, it should be noted that, while the clustering algorithm according to invention principles is particularly advantageous in the case that the number of curves is small (e.g. equal to or less than 8), the algorithm is operable on any number of curves and an amount of time and processing power to execute the algorithm increases as a number of curves increase. In this manner, the clustering algorithm advantageously need not use a result of a prior clustering analysis because, given an arbitrary cluster number, the clustering operation according to invention principles begins de novo and need not rely on other previously determined clustering results. Further, the predetermined (e.g. small) number of melt curves advantageously enables application of brute force search techniques which are guaranteed to find the global optimum solution for the clustering of the finite number of melt curves.

Figure 3:
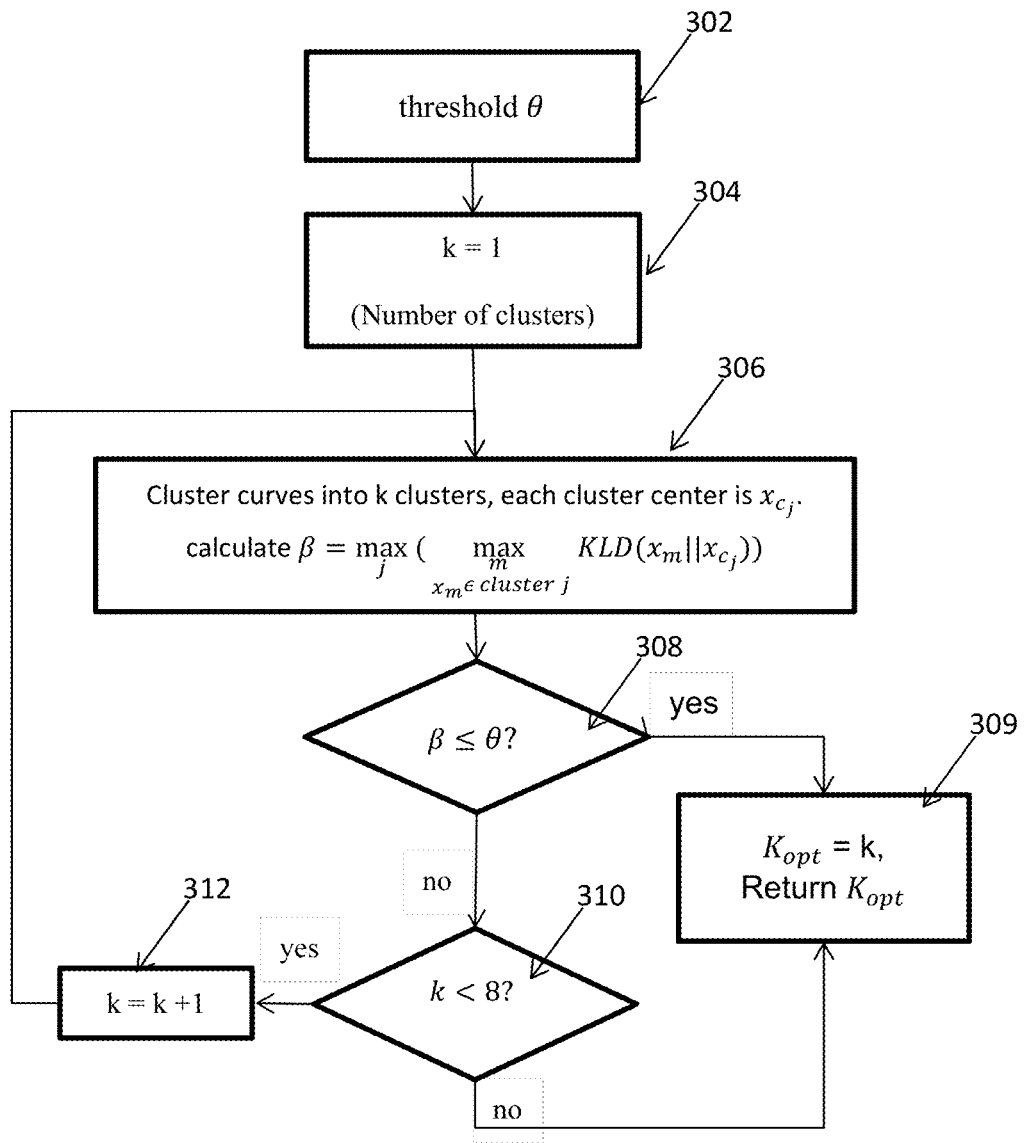
FIG. 3 illustrates a clustering algorithm according to invention principles.

FIG. 3 is a flow diagram detailing an algorithm for determining an optimal number of clusters into which a finite number of melt curves obtained from thermal melt processing are to be grouped. In one embodiment, the number of melt curves to be processed by the clustering algorithm is equal to a number of channels on a device having nucleic acid samples contained therein and which have undergone PCR and melt processing to generate melt curves showing the relationship between fluorescence and temperature for the sample and indicating temperatures at which the nucleic acids in the respective channel have been denatured. In one embodiment, the device 102 includes eight channels and can produce up to eight melt curves on a single run. The remaining description will presume that the clustering algorithm will be operating on eight data object each representing a respective melt curve derived from one of the eight channels in a device 102. However, this is described for purposes of example only and a device having a number of channels greater than or less than eight may be used and the clustering algorithm may operate on a total number of melt curves equal to a total number of channels.

The clustering algorithm according to invention principles may cluster any type of melt curve including the raw melt curve produced after melt processing or on processed melt curve. Examples of a processed melt curve which can be supplied as an input value for the clustering algorithm include a background curve, a normalized melt curve, a derivative melt curve, a negative derivative melt curve and/or a smoothed melt curve. The types of processed melt curves described herein are done so for purposes of example only and any raw melt curve data having been processed using one or more filters may be supplied as an input for clustering purposes according to invention principles.

Given eight melt curves derived from a device having eight channels, $x_1, x_2, \ldots, x_8$, the clustering algorithm normalizes each curve such that each sum of the curve equals to 1. Each curve is then treated as a probability distribution and a dissimilarity value is calculated for each pair of melt curves. In one embodiment, the dissimilarity value is calculated with a KL-divergence value according to Equation 1:

$$KLD(x_i \| x_j) = \sum_t x_i(t) \ln \frac{x_i(t)}{x_j(t)} \quad (1)$$

where is the data point index of each curve. The dissimilarity value calculated for each curve pair represents a non-symmetric measure of the mutual information shared by one curve and a reference curve. A dissimilarity value approaching 0 indicates that the two curves are similar to one another. However, the KLD value equals to 0 between two melt curves when the curves are the same. In other words, the value $KLD(x_i \| x_j) = 0$ only if $x_i = x_j$.

Now that the melt curve data has been preprocessed, the algorithm of FIG. 3 determines an optimal best number of clusters $K_{opt}$ of the given curves. In step 302, an acceptable dissimilarity threshold $\theta$ is set. The threshold $\theta$ represents a value that defines how similar the curves to be included in a particular cluster must be to one another in order to be grouped in the particular cluster. In one embodiment, the threshold $\theta$ is a largest acceptable KL-divergence value within each cluster. In certain embodiments, threshold $\theta$ is a predetermined value (e.g. 0.0335). In other embodiments, threshold $\theta$ may be selectively configurable by a user. For example, the clustering algorithm may generate a data object representing a user interface display screen including at least one user selectable image element that enables the user to selectively define a value for threshold $\theta$. In one example, the user selectable image element may be a slider bar wherein each position along a length (or height) of the slider bar may represent a different dissimilarity value and user can set an acceptable value for threshold $\theta$. In other embodiments, the user interface display may include a number of selectable image elements representing candidate threshold $\theta$ values which may be selected in any known manner (e.g. drop down menu, image element buttons, check boxes, etc.). In another embodiment, the ability to define the value for threshold $\theta$ may be available at any time during the clustering process whereby input of a new value for threshold $\theta$ results in automatic recalculation and clustering of the melt curves as will be discussed hereinafter.

In step 304, a number of clusters k is set equal to 1 and the eight melt curves are clustered into k clusters from k=1. Based on the clustering result which may be derived from the clustering algorithm in FIG. 5 described below, in step 306, we calculate a cluster quality value $\beta$ which represents a maximum dissimilarity value between clusters by determining a maximum divergence between each curve and a given curve at a center of the cluster where $c_j$ is the index of the curve which is the center of cluster j and $x_i$ is the i-th curve, and $x_{c_j}$ is the curve which is the center of cluster j. In step 308, the algorithm queries if the value of $\beta \leq \theta$. If the result of the query in step 308 is positive (YES in 308), k is set as $K_{opt}$ in step 310. Once the value of $K_{opt}$ has been set, it will be used as an input to the algorithm in FIG. 5. If the result of the query in 308 is negative (NO in 308) indicating that a value for $\beta > \theta$, a further query is performed in step 309 to determine if the value of k is less than a total number of melt curves (e.g. k<8). If the result of the query in step 309 is negative (NO in 309), then the algorithm sets k as the value for $K_{opt}$. If the result of the query in step 309 is positive (YES in 309), a value of k is incremented by one and the algorithm reverts to step 306 to perform the clustering into a number of clusters equal to k+1 (in this first iteration of the algorithm it would be 2). The algorithm of FIG. 3 repeats itself until it is determined that a particular number of clusters results in a cluster quality value that is less than a value of threshold $\theta$ representing a least dissimilarity value that is acceptable for each curve within a particular cluster. An exemplary set of pseudo code that may be used as another embodiment is shown in FIG. 4.

The algorithmic operation described in FIGS. 3 and 4 represent a brute force search for the best center points for the optimal number of clusters to be used for a set of eight melt curve data derived from a panel run using a device. The brute force clustering approach described herein enables each clustering operation to start from scratch due to the predetermined (e.g. small) number of curves to be clustered resulting in a globally optimum solution. In an embodiment where there is a larger number of curves, alternative clustering processes may be used in order to reduce the computational cost during the clustering of the melt curve data. In one embodiment, a K-medioids clustering algorithm could be employed. The result, while computationally more efficient, would not necessarily reach the globally optimal solution of a number of clusters for the given set of melt curve data as compared to the brute force approach preferred herein. In addition to limiting the set of input curves to a predetermined (e.g. small) set of curves, the brute force clustering approach is made computationally more efficient based on the dissimilarity value (KLD divergence value) calculated for each curve as compared to each other curve and stored in memory as a dissimilarity data structure. In this manner, the clustering algorithm can use the information stored in the dissimilarity data structure to efficiently determine a respective curves position within a particular cluster having a particular center associated with any of the other curves in the predetermined (e.g. small) set of data.

Additionally a hybrid brute-force non-brute-force method may be employed to perform brute force searching for a small or large number of clusters relative to the number of curves. The brute force methods may be applied selectively, for example, based on a priori knowledge of the maximum number of known genotypes for the alleles under analysis. Alternatively a non-brute-force method such as k-mediods may be used when the number of clusters produces prohibitively many clustering combination to examine if a brute-force method were to be used. This approach is usually practical because the number of expected genotypes is typically small.

Figure 5:
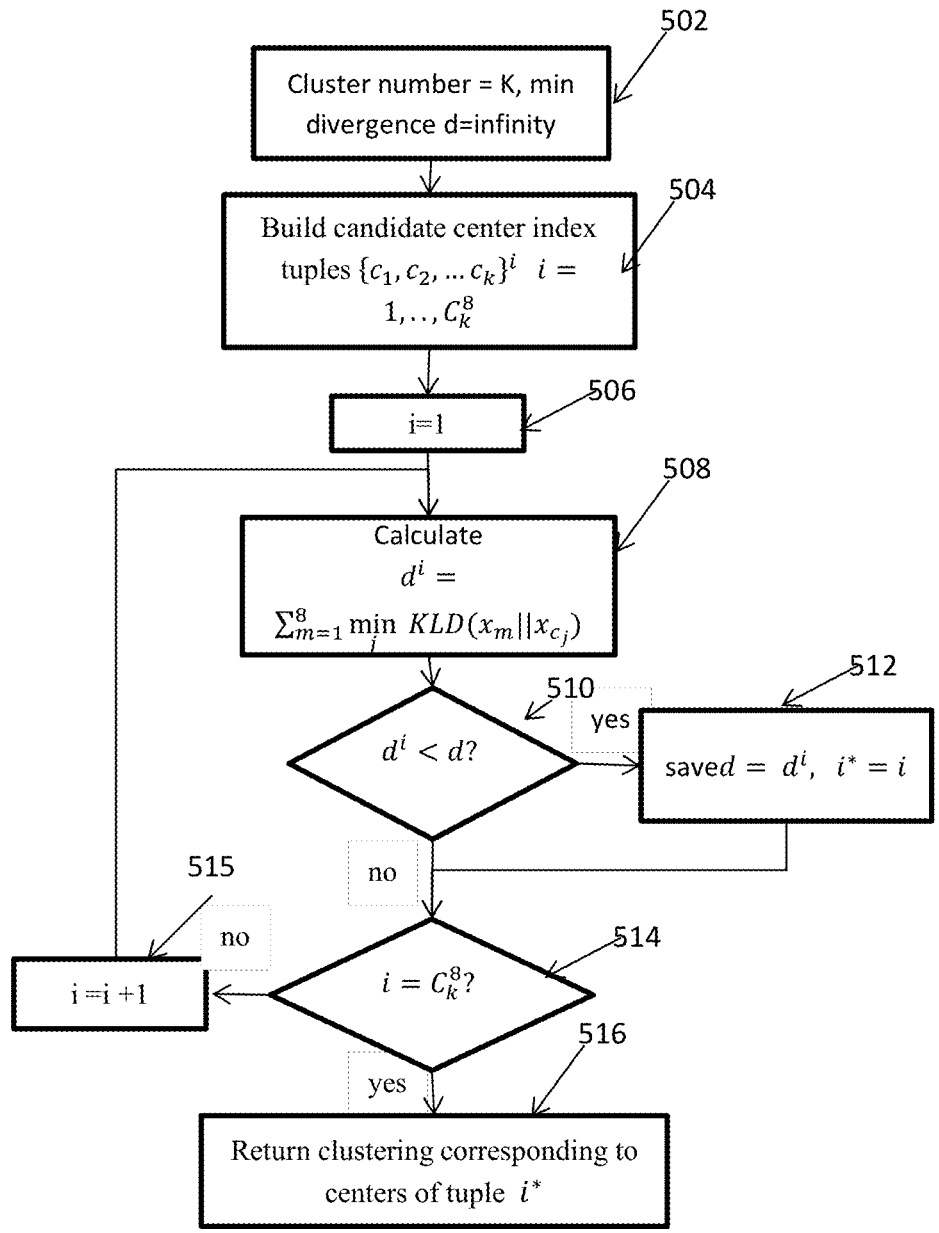
FIG. 5 illustrates a clustering algorithm according to invention principles.

FIG. 5 illustrates another aspect of the clustering algorithm according to invention principles. In step 502, the algorithm is initialized and sets a cluster number to an initial value and sets this value equal to K and sets a minimum divergence value d equal to infinity. In one embodiment, K is set equal to 1 and once all conditions in FIG. 5 as discussed below are satisfied, the clustering results from FIG. 5 will be used in step 306 in FIG. 3 discussed above to find the value $K_{opt}$. In another embodiment, K is set equal to $K_{opt}$ as determined by the algorithm shown above in FIG. 4 whereby the ultimate output of the FIG. 5 algorithm as discussed below will be clustering results having $K_{opt}$ clusters. In step 504, the algorithm builds candidate center index tuples as follows: $\{c_1, c_2, \ldots c_k\}^i$ i=1, ..., $C_k^8$ where the number of the possible candidates C is calculated by Equation 2:

$$C_K^8 = \frac{8!}{k!(8-k)!} \quad (2)$$

Since the number of melt curves being input to the algorithm is fixed as eight based on the number of channels of the device having nucleic acid samples therein and which underwent melt processing, the possible candidates number for K from 1 to 8 is 8, 28, 56, 70, 56, 28, 8, 1, respectively according to equation (2). This is the number of ways one can choose k cluster centers from a set of 8 curves for k=1 to 8. To find the best K cluster centers, the algorithm employs a brute force cluster method which is guaranteed to find the global optimum solution. For example, given K cluster centers, the other 8-K curves are assigned to their most similar center according to the lowest dissimilarity value of KLD.

In step 506 an index for a given set of cluster center candidates, i, is set equal to 1 and in 508 a cost is calculated by summing all the $KLD(x_m \| x_{cj})$ if curve m is assigned to cluster center j. The final best K cluster centers will be the one with the minimum cost. The cost is determined in step 508 where a divergence value for cluster center candidate set i is calculated by summing the minimum dissimilarity value (min KLD value) for each curve relative to the candidate cluster center curves. In step 510, the algorithm queries whether the cost for the cluster center candidate set is less than the minimum cost observed thusfar (e.g. is $d^i < d$). If the result of the query in 510 is positive (YES in 510), the algorithm stores, in step 512, the value of $d^i$ as d and i*=I (it stores the minimum cost observed up to that point, and the cluster center candidate set that generated that cost). If the query in step 510 is negative (NO in 510) or, after the data values are set in step 512, the algorithm queries, in step 514, whether the value of i is equal to the total number of candidate cluster centers sets. If the result of the query in 514 is positive (YES in 514), the clustering is returned corresponding to the centers of tuple i*. If the query in step 514 is negative, the value of i is incremented by one and the algorithm reverts back to step 508 to evaluate the cost of the next cluster centers candidate set. The advantage of this algorithm is its efficiency by only calculating the KLD divergence once for different K number and possible candidate centers. Although it's a brute force searching method, the search is done by checking the KLD divergence as a lookup table which is not computational expensive.

In one embodiment, there is therefore provided a system for determining cluster centers for curves associated with biological reactions on a device, the system comprising: (i) a device having at least two biological samples; (ii) a thermal system in communication with the device, the thermal system controlling a temperature within the device causing a biological reaction in each of the biological samples; (iii) one or more processors in communication the device; and (iv) a storage including instructions that, when executed by the one or more processors: (a) generate at least one curve indicative of the biological reaction in each of the biological samples, each curve representing a change in a physical parameter associated with the biological sample as a function of the temperature within the device; (b) calculate an optimal cluster number for the generated curves; (c) build at least one tuple containing cluster centers represented by the curves, wherein the number of cluster centers in each tuple equals the optimal cluster number and each optimal cluster number corresponds to a specific number of tuples; (d) for each tuple, calculate a cost value indicative of curves outside of the tuple fitting into clusters associated with the cluster centers in the tuple; and (e) return cluster centers in a tuple having a minimum cost value.

Similarly, in another embodiment, there is provided a method for determining cluster centers for curves associated with biological reactions on a device having at least two biological samples and which includes a thermal system in communication with the device that controls a temperature within the device causing a biological reaction in each of the biological samples, the method comprising: (a) generating at least one curve indicative of the biological reaction in each of the biological samples, each curve representing a change in a physical parameter associated with the biological sample as a function of the temperature within the device; (b) calculating an optimal cluster number for the generated curves; (c) building at least one tuple containing cluster centers represented by the curves, wherein the number of cluster centers in each tuple equals the optimal cluster number and each optimal cluster number corresponds to a specific number of tuples; (d) for each tuple, calculating a cost value indicative of curves outside of the tuple fitting into clusters associated with the cluster centers in the tuple; and (e) returning cluster centers in a tuple having a minimum cost value.

Figure 6A:
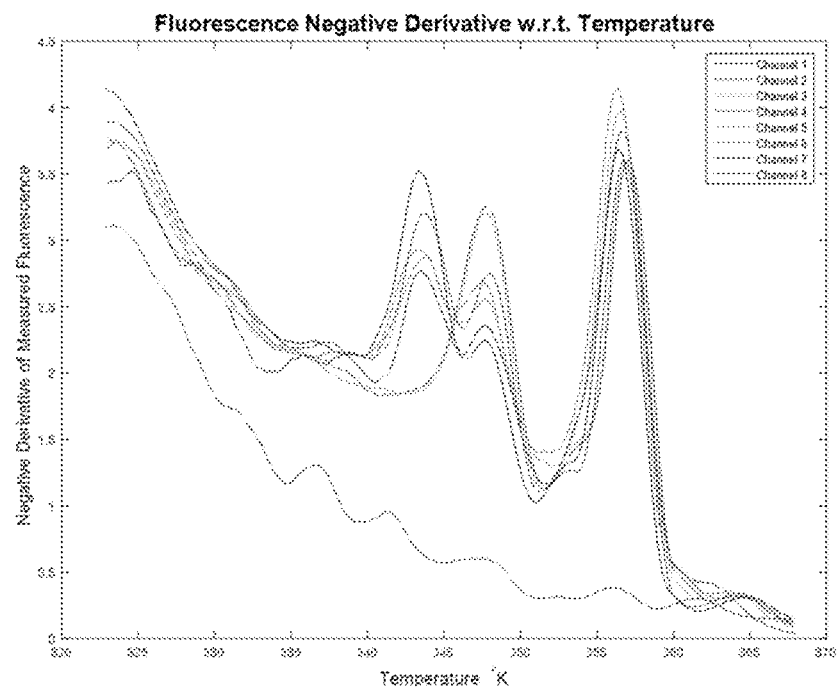
FIGS. 6A-6B illustrate raw melt curve data and normalized melt curve data, respectively, from a first assay of the WARAFARIN data set according to invention principles.
Figure 6B:
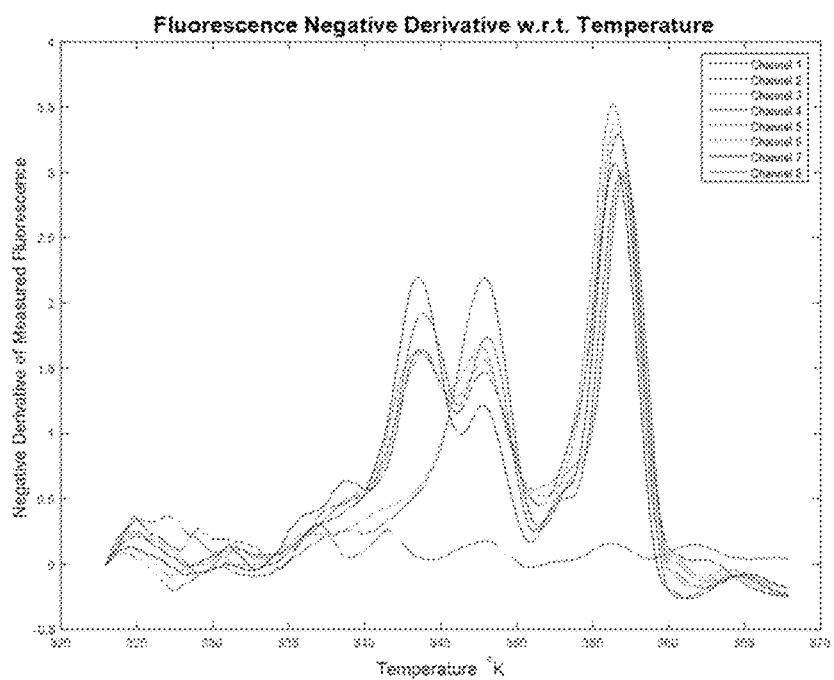

FIGS. 6A-6D depict the raw melt curve data and normalized melt curve data derived from two assays in the WARFARIN data set wherein dissimilarity values between the curves have been calculated as discussed above. FIG. 6A shows an unprocessed plot of melt curves depicting the negative derivative of measured fluorescence relative to temperature and FIG. 6B shows the curves from FIG. 6A after undergoing normalization. FIG. 7A depicts the value of the divergences between each curve for the WARFARIN data set shown in FIG. 6A/6B. FIG. 7A illustrates the dissimilarity values for each curve relative to each other curve as compared the threshold of acceptable dissimilarity depicted in the legend adjacent thereto. As discussed above in FIG. 3, the acceptable dissimilarity threshold is set equal to 0.035 and the result is that optimal number of clusters for the melt curves in FIGS. 6A/6B is 4 according to the algorithm described in FIG. 3.

Figure 6C:
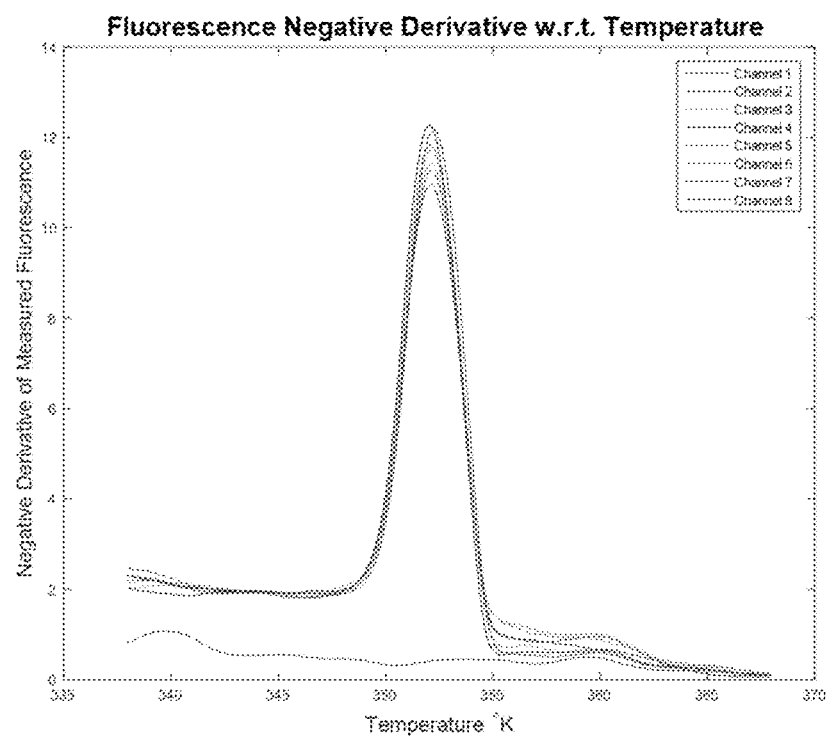
FIGS. 6C-6D illustrate raw melt curve data and normalized melt curve data, respectively, from a second assay of the WARAFARIN data set according to invention principles.
Figure 6D:
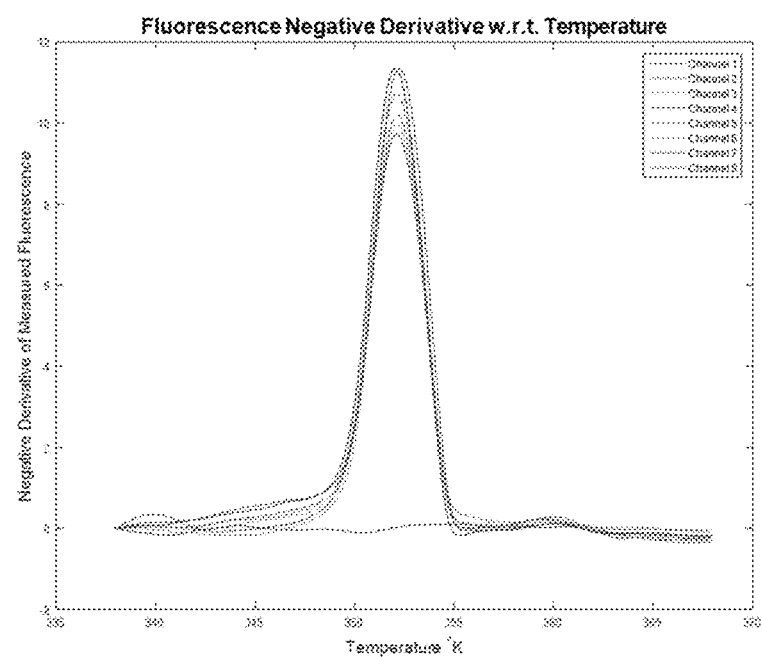
Figure 7A:
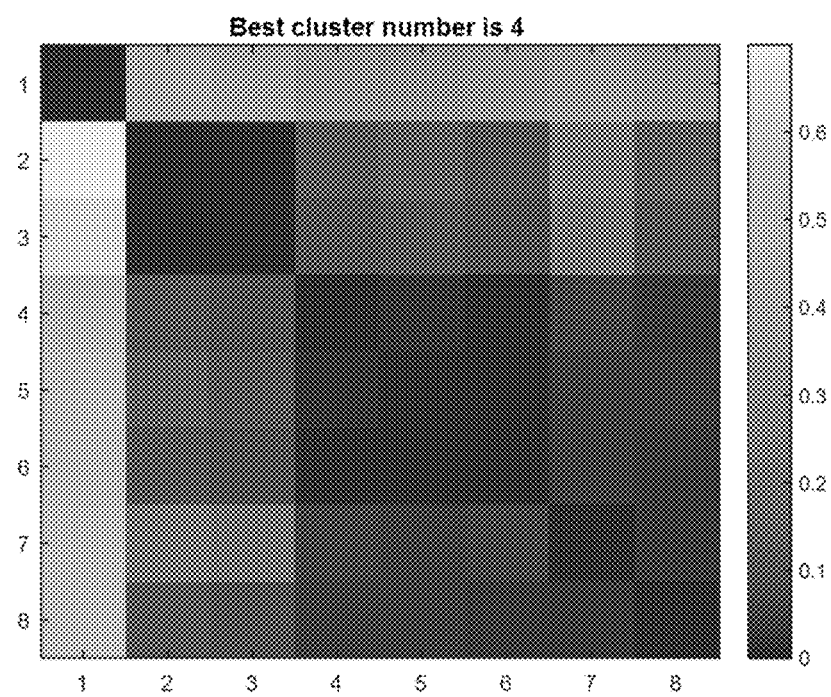
FIGS. 7A-7B illustrate optimal cluster numbers from the assays of FIG. 6A/6B and FIG. 6C/6D, respectively, according to invention principles.
Figure 7B:
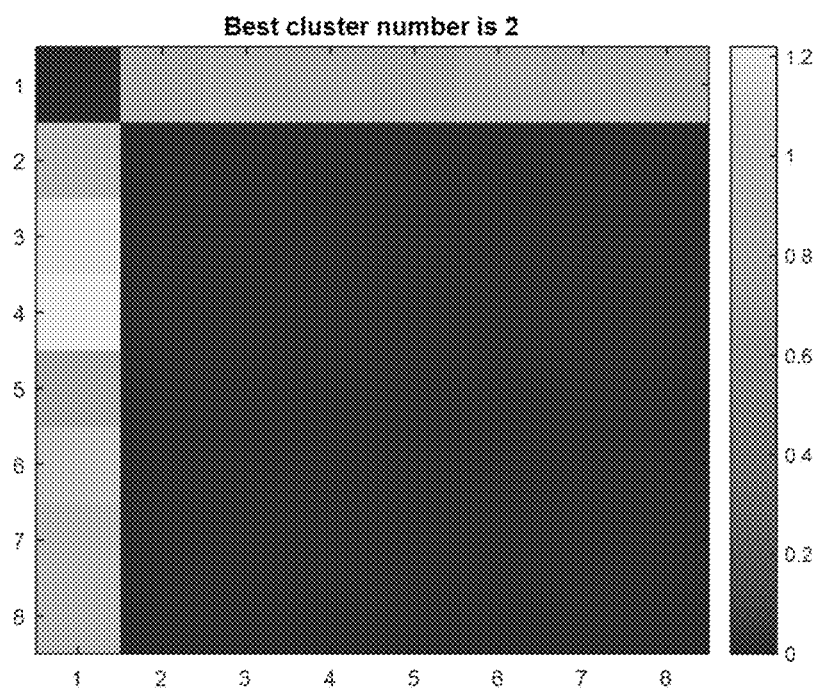

FIG. 6C illustrates raw melt curves derived from a second assay from the WARFARIN data set having dissimilarity values between curves calculated as above and FIG. 6D depicts the curves of FIG. 6C after normalization. FIG. 7B depicts the value of divergences between each curve for this particular assay in the WARAFARIN data set shown in FIG. 6C/6D. FIG. 7B illustrates the dissimilarity values for each curve relative to each other curve as compared the threshold of acceptable dissimilarity depicted in the legend adjacent thereto. As discussed above in FIG. 3, the acceptable dissimilarity threshold is set equal to 0.035 and the result is that optimal number of clusters for the melt curves in FIGS. 6C/6D is 2 according to the algorithm described in FIG. 3.

Figure 8A:
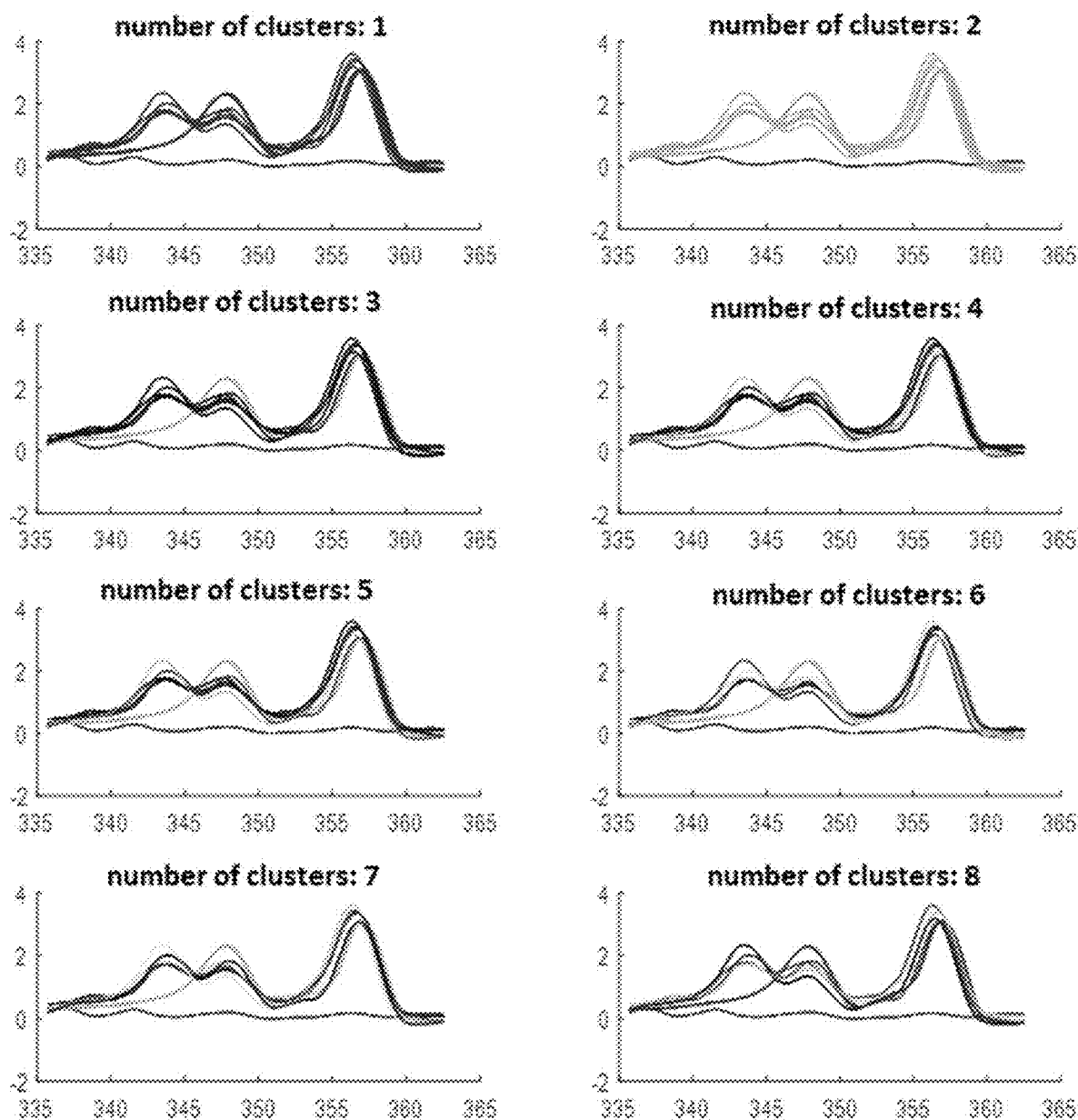
FIGS. 8A-8B illustrate exemplary user interface display images according to invention principles. a plot of n-ellipses that each contain three standard deviations of the two-dimensional data points representing the dynamic profiles, with one n-ellipse for each genotype.
Figure 8B:
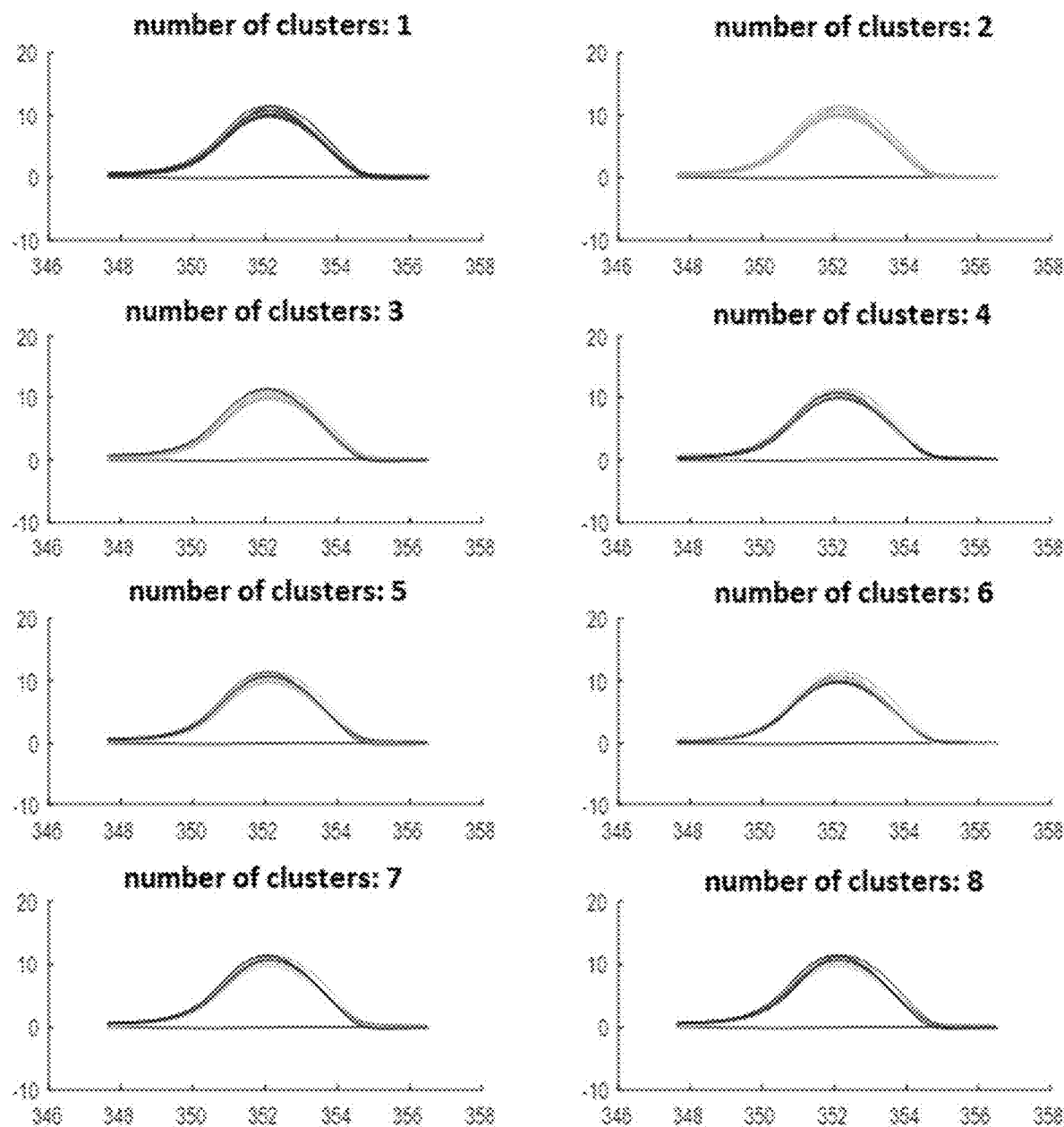

In certain instances, despite mathematically calculating the global optimum solution for an optimal number of clusters for a particular set of melt curve data, user verification that the determined optimal cluster number, $K_{opt}$, is correct may be required due to ambiguity resulting from the shape and scale of the distribution of particular points in the melt curve data set and the desired clustering resolution of the user. Thus, to further improve the ability to identify the optimal number of clusters, the clustering algorithm generates user interface data objects that display the clustering results including the optimal number of clusters and less than optimal clustering results. In one embodiment, the user interface is generated to include the clustering according to a number of cluster values defined as $K_{opt}-1$, $K_{opt}$ and $K_{opt}+1$, so users can visually compare the clustering results and choose the best one for their interests. In certain embodiments, the user interface may generate a UI data objecting including individual plots for simultaneously displaying clustering results for a number of clusters equal to a total number of melt curves in the data set. An example of a UI including such a type of display is shown in FIGS. 8A and 8B wherein there are eight discrete image elements representative of clustered melt curves. FIG. 8A shows the clustering of the normalized negative derivative melt curve of FIG. 6A whereas FIG. 8B shows the normalized negative derivate of the melt curves in FIG. 6C. Each image element represents a different number of clusters ranging from a lowest possible number of clusters (1) to the highest possible number of clusters (8) wherein the possible number of cluster groups is equal to the number of melt curves input to the algorithm. In each image element representing a number of clusters, the curves associated with a respective cluster are depicted using a common visual indicator. For example, if the number of clusters is 4, then there will be four groups of melt curves and each curve in a particular group will have a common appearance (e.g. same color or same line pattern).

Figure 9A:
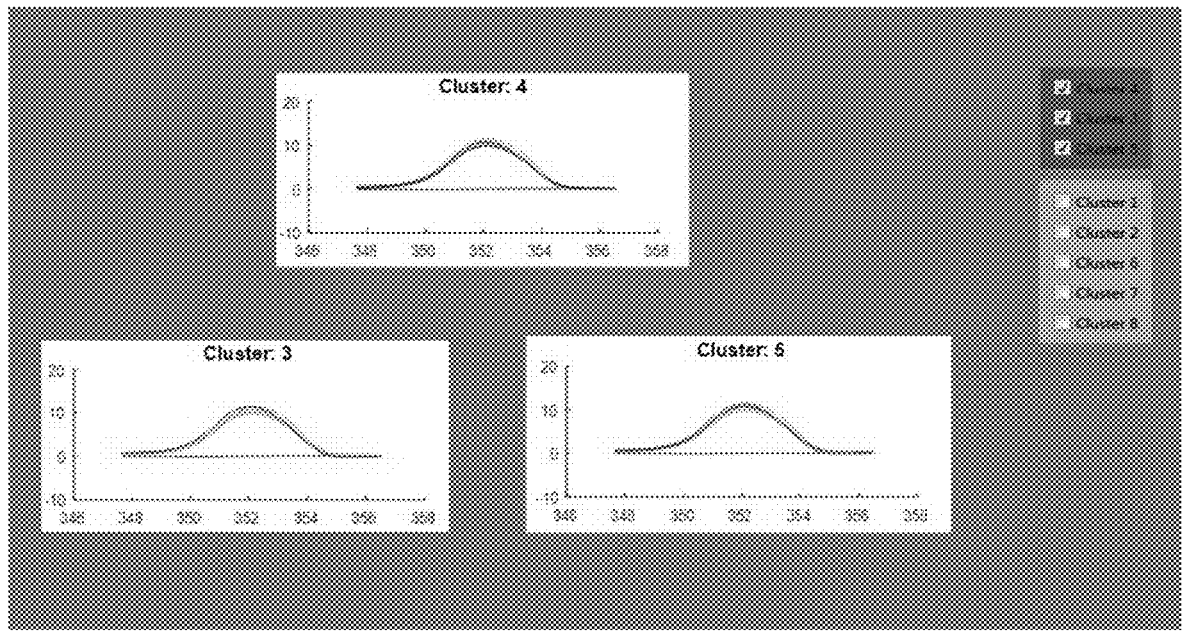
FIG. 9A-9B illustrate exemplary user interface display images according to invention principles.

FIG. 9A is a further exemplary user interface generated by the clustering algorithm according to invention principles. As shown herein, the clustering algorithm generates a set of recommended cluster candidates which include cluster numbers equal to $K_{opt}-1$, $K_{opt}$ and $K_{opt}+1$. As shown in FIG. 7A, $K_{opt}$ is 4, so the set of recommended clusters includes both $K_{opt}-1$ (3) and $K_{opt}+1$ (5). The UI generated by the clustering algorithm includes image elements representing these three clustering groups. In one embodiment, each curve that is part of a respective cluster is depicted using a same visual indicator (e.g. color, line pattern, etc.).

Figure 9B:
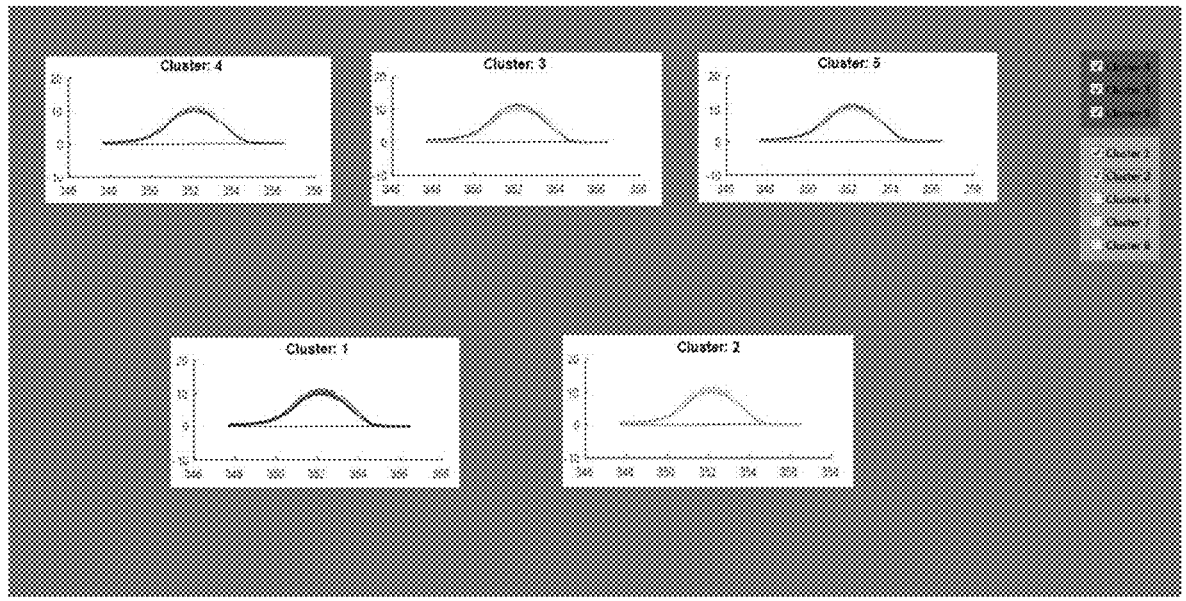

In another embodiment, the clustering algorithm generates candidate cluster selection image elements which presents, to the user, the recommended set of clusters depicted using a first visual indicator wherein each member of the set of recommended clusters includes a selection box to one of select of de-select the respective clustering result from being displayed within the UI window of FIG. 9A. In addition to the set of recommended clusters, image elements representing all other available clusters is generated and depicted to a user via a second visual indicator. These may be determined as non-recommended clusters because their dissimilarity measures may be numerically above the acceptable threshold dissimilarity value but still may be of interest to a user when verifying the number of optimal clusters for a particular data set. As such, each member of the non-recommended clusters also includes a selection box enabling a user to select or deselect a particular cluster for display thereof. An example of this is shown in FIG. 9B wherein a non-recommended clustering group includes one cluster, two clusters, six clusters, seven clusters and eight clusters and a user has selected the one cluster plot and two cluster plot to be displayed within the user interface along with the set of recommended clusters. The clustering algorithm can dynamically update the user interface based on the selection or deselection within the user interface. In certain other embodiments, a position of a respective clustering data plot within a user interface may be determined based on its value relative to $K_{opt}$ such that an ordered display of the clusters may be provided.

Figure 10:
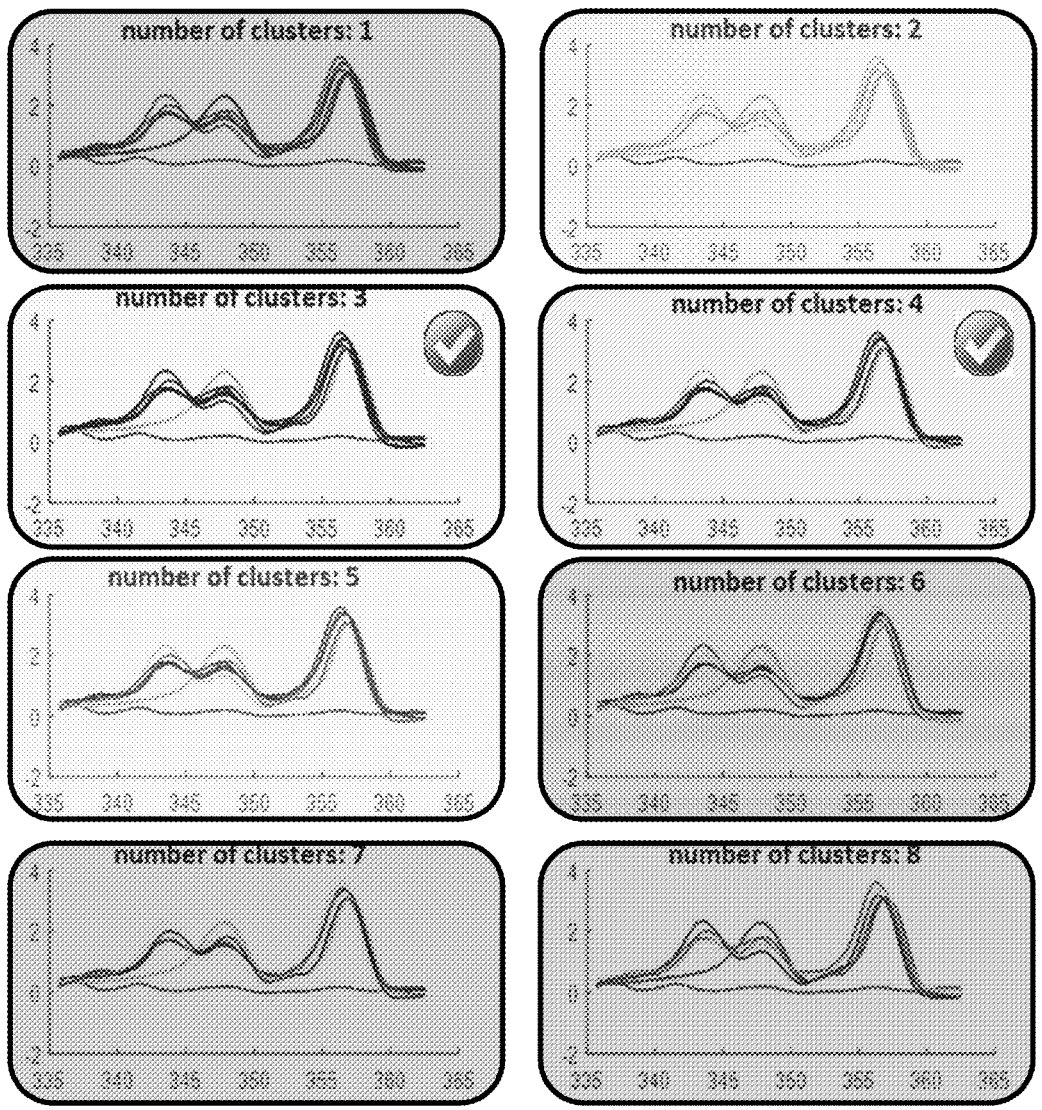
FIG. 10 illustrates an exemplary user interface display image according to invention principles.

FIG. 10 is yet another exemplary user interface able to be generated by the clustering algorithm whereby some or even all possible cluster graphs are displayed and the cluster corresponding to $K_{opt}$ is shown in a first color and including a check mark indicating that the cluster is part of the recommended set of clusters. The remaining recommended clusters may also be visually depicted in the same manner and all other clusters may be depicted using a second color different from the first color.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for determining cluster centers for curves associated with biological reactions on a device having at least two biological samples, the method comprising:

providing a device having at least two biological samples;

providing a thermal system in communication with the device, the thermal system controlling a temperature within the device causing a biological reaction in each of the biological samples, wherein the biological reaction is a thermal melt reaction;

providing a controller in communication with the device, the controller providing instructions for:
generating at least one curve indicative of the biological reaction in each of the biological samples, each curve representing a change in a physical parameter associated with the biological sample as a function of the temperature within the device;
calculating an optimal cluster number for the generated curves;
building at least one tuple containing cluster centers represented by the curves, wherein the number of cluster centers in each tuple equals the optimal cluster number and each optimal cluster number corresponds to identified tuples;
for each tuple, calculating a cost value indicative of curves outside of the tuple fitting into clusters associated with the cluster centers in the tuple; and
returning cluster centers in a tuple having a minimum cost value.

2. The method of claim 1, further comprising clustering each curve into a cluster having an identified cluster center by calculating a dissimilarity value between the curve and each cluster center and selecting the cluster having the cluster center providing a minimum total dissimilarity.

3. The method of claim 1, further comprising normalizing each of the curves, wherein a sum of each curve equals to 1.

4. The method of claim 1, further comprising calculating the optimal cluster number by comparing a total dissimilarity calculated for each pair of curves to a predetermined threshold.

5. The method of claim 4, wherein the dissimilarity value for curves $x_i$, $x_j$ is KL-divergence (KLD) calculated as $$KLD(x_i \| x_j) = \sum_t x_i(t) \ln \frac{x_i(t)}{x_j(t)},$$

where t is the data point index of each curve.

6. The method of claim 5, wherein the cost value for each tuple is calculated as:

$$\sum_{m=1}^{number\ of\ biological\ samples} \min_j KLD(x_m \| x_{c_j}),$$

where $x_{c_j}$ is a cluster center.

7. The method of claim 1, further comprising calculating the optimal cluster number by determining cluster centers for each identified cluster number, calculating a cluster quality value for the cluster centers, and comparing the cluster quality value to a predetermined threshold.

8. The method of claim 7, wherein the cluster quality value is calculated as $$\beta = \max_j \left( \max_{\substack{m \\ x_m \in cluster\ j}} KLD(x_m \| x_{c_j}) \right),$$

wherein the cluster number is incremented if $\beta$ is less or equal to the predetermined threshold.

9. The method of claim 1, wherein the number of tuples for K clusters is calculated as $$C_K^8 = \frac{8!}{K!(8-K)!}.$$

10. The method of claim 1, wherein each biological sample in the microfluidic device is a DNA sample, and the curve indicative of the biological reaction is a DNA melt curve.

11. The method of claim 10, wherein the physical parameter associated with the DNA sample is a fluorescence signal changing as the DNA denatures.

12. The method of claim 11, further comprising the thermal system increasing the temperature within the microfluidic device at a constant rate to cause a DNA denaturation.

13. The method of claim 10, further comprising providing a detection system, the melt curves being generated based upon images of the DNA samples captured by the detection system.

14. The method of claim 1, wherein the biological samples are in a channel of the device.

15. A method for determining cluster centers for curves associated with biological reactions on a device, the method comprising:
providing a device having at least two biological samples;
providing a thermal system in communication with the device, the thermal system controlling a temperature within the device causing a biological reaction in each of the biological samples, wherein the biological reaction is a thermal melt reaction;
providing a controller in communication with the device;
wherein the controller receives data representing at least one curve associated with a biological sample having undergone the biological reaction occurring in the device, each curve representing a change in a physical parameter associated with the biological sample as a function of a temperature within the device;
wherein the controller provides instructions to:
calculate an optimal cluster number for the generated at least one curves;
build at least one tuple containing cluster centers represented by the at least one curves, wherein the number of cluster centers in each tuple equals the optimal cluster number and each optimal cluster number corresponds to identified tuples;
for each tuple, calculate a cost value indicative of curves outside of the tuple fitting into clusters associated with the cluster centers in the tuple; and
return data representing cluster centers in a tuple having a minimum cost value.

16. The method according to claim 15, wherein the device includes a user interface, and wherein the method further comprises
generating a user interface display image including at least one image element representing the returned data representing cluster centers.

17. A system for determining cluster centers for curves associated with biological reactions on a device, the system comprising:
a device having at least two biological samples;
a thermal system in communication with the device, the thermal system controlling a temperature within the device causing a biological reaction in each of the biological samples, wherein the biological reaction is a thermal melt reaction;
one or more processors in communication the device;
a storage medium including instructions, that when executed by the one or more processors:
generate at least one curve indicative of the biological reaction in each of the biological samples, each curve representing a change in a physical parameter associated with the biological sample as a function of the temperature within the device;
calculate an optimal cluster number for the generated curves;
build at least one tuple containing cluster centers represented by the curves, wherein the number of cluster centers in each tuple equals the optimal cluster number and each optimal cluster number corresponds to of identified tuples;
for each tuple, calculating a cost value indicative of curves outside of the tuple fitting into clusters associated with the cluster centers in the tuple; and
return cluster centers in a tuple having a minimum cost value.

* * * * *